(12) United States Patent
Griesbach, III

(10) Patent No.: US 6,615,837 B1
(45) Date of Patent: Sep. 9, 2003

(54) EDGE WEIGHTED SURGICAL DRAPE

(75) Inventor: Henry L. Griesbach, III, Clarkston, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 10/326,181

(22) Filed: Dec. 20, 2002

(51) Int. Cl.⁷ ............................................... A61B 19/00
(52) U.S. Cl. ...................................... 128/849; 128/852
(58) Field of Search ................................. 128/849–856

(56) References Cited

U.S. PATENT DOCUMENTS

| | | |
|---|---|---|
| 3,359,569 A | 12/1967 | Rotanz et al. |
| 3,721,999 A | 3/1973 | Goya et al. |
| 4,535,481 A | 8/1985 | Ruth-Larson et al. |
| 4,942,987 A | 7/1990 | Stackhouse |
| 5,253,642 A | 10/1993 | Stackhouse et al. |
| 5,464,024 A | 11/1995 | Mills et al. |
| 5,471,999 A | 12/1995 | Mills |

FOREIGN PATENT DOCUMENTS

WO  01/92619 A2  12/2001

*Primary Examiner*—Michael A. Brown
(74) *Attorney, Agent, or Firm*—Scott B. Garrison

(57) ABSTRACT

The invention relates to a nonwoven surgical drape made of a non-cellulose containing base sheet having a source of additional weight uniformly distributed along side edges of the drape. The source of additional weight may have a mass per unit length between about three times and about eight times the basis weight of the base sheet.

16 Claims, 3 Drawing Sheets

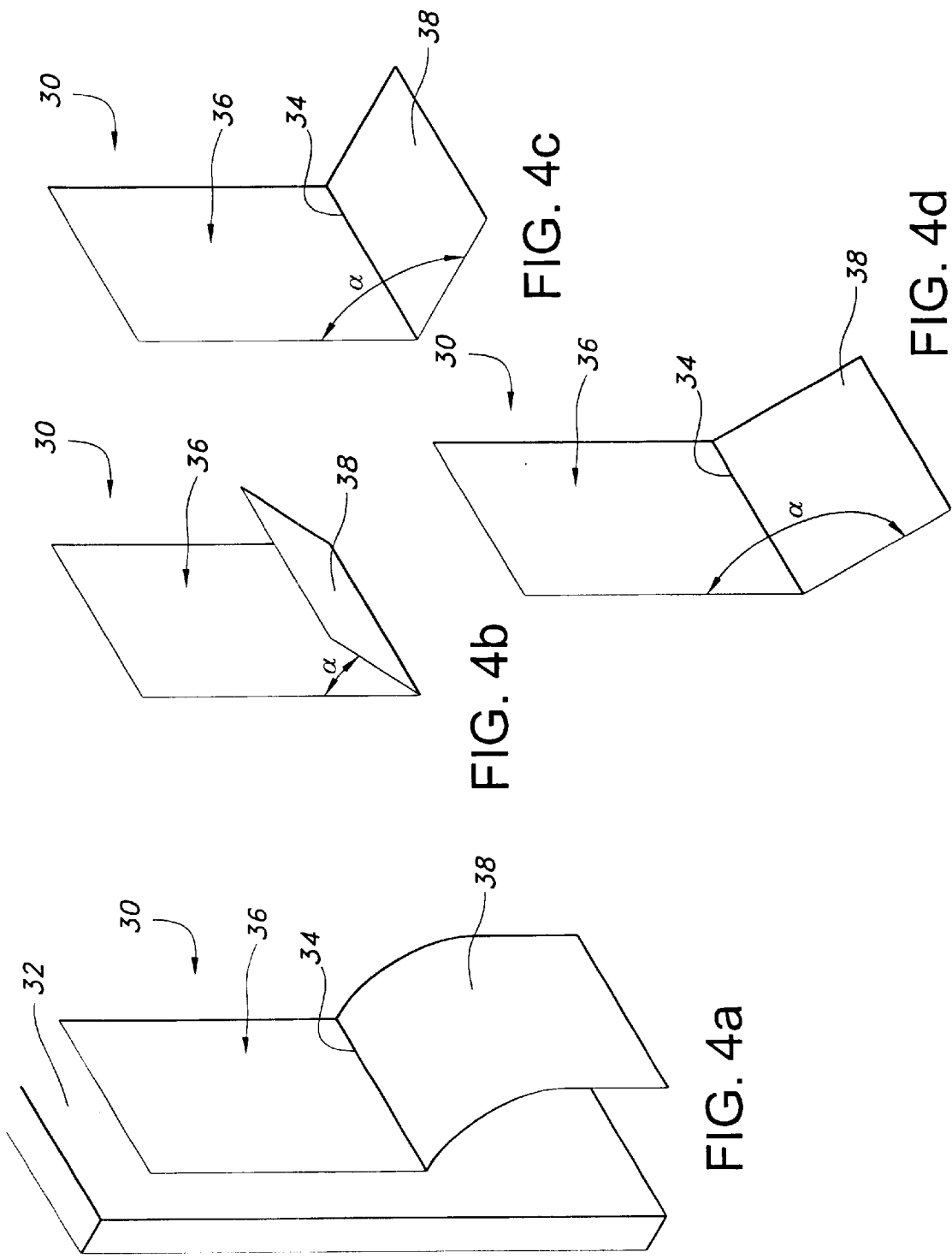

EDGE WEIGHTED SURGICAL DRAPE

BACKGROUND

The present invention relates to surgical drapes and the like.

Surgical drapes are used during surgical procedures, in part, to provide a sterile field about the surgical site and during other treatment procedures requiring the maintenance of a sterile environment. When used during surgery, drapes prevent blood and other bodily fluids from cross contaminating the sterile field.

Various types of surgical drapes have been used to keep a surgical site on a patient sterile during a surgical procedure. Traditionally, surgical drapes were linen or woven cloth, and were sterilized after each use for reuse. More recently, disposable drapes have been introduced, in which nonwoven paper or fabric forms a substantial part of the drape. A reinforcement area is often placed around a fenestration opening or edge in disposable surgical drapes to provide structural strength and to absorb bodily fluids from a surgical site. Many disposable drapes include a number of layers of different materials for the drape area and reinforcement area, with each layer providing a different property to the drape. For example, spunbond fabrics, meltblown fabrics, and polymer films have been used as layers in disposable drapes.

Many different shapes of surgical drapes have been proposed, often depending upon the specific surgical procedure to be performed. For example, the shape of the drape was often specifically designed to fit around a specific surgical site on the body. In some cases, a fenestration opening was provided through a drape to allow medical personnel access to the surgical site, whereas the remaining sheet portion of the drape would cover the rest of the body and table. Often, several drapes were used in combination to cover a patient. In some cases, several rectangular drapes, often called universal drapes, were laid over the patient in a pattern providing an opening through which the medical personnel could access the surgical site while also covering the remainder of the patient's body and the table.

Packaging of the drapes requires that the drape be folded numerous times. The drapes upon removal from the packaging are creased at those areas corresponding to the fold lines. The creases have a tendency to cause the drape to remain partially folded even when the drape is placed over a patient. Direct manipulation of the drape is often required to completely unfold the drape. This is especially the case the closer the crease comes to an edge of the drape. A better method is needed to assist in unfolding the drape.

SUMMARY OF THE INVENTION

As such, one aspect of the present invention discloses a nonwoven surgical drape made of a non-cellulose containing base sheet including a top edge, a bottom edge, at least two side edges, and a source of additional weight uniformly distributed along the side edges. The source of additional weight may have a mass per unit length between about three times and about eight times the basis weight of the base sheet. In some embodiments the source is within about 2 cm to about 5 cm of each side edge. In other embodiments the source is within about 0.8 cm of each side edge. In still other embodiments the source is within about 0.8 cm to about 2 cm of each side edge. Some embodiments utilize a source of additional weight that is uniformly divided along each side edge. Other embodiments utilize a flexible material adjoined to each side edge as an added source of weight. The source of additional weight may include a bead of hot melt adhesive, a flexible filled-polymer band, and/or a nonabsorbent material.

BRIEF DESCRIPTION OF THE DRAWINGS

FIGS. 4a–d shows a diagram of the vertical unfold testing performed on sample specimens.

DESCRIPTION OF THE INVENTION

Figure 1:
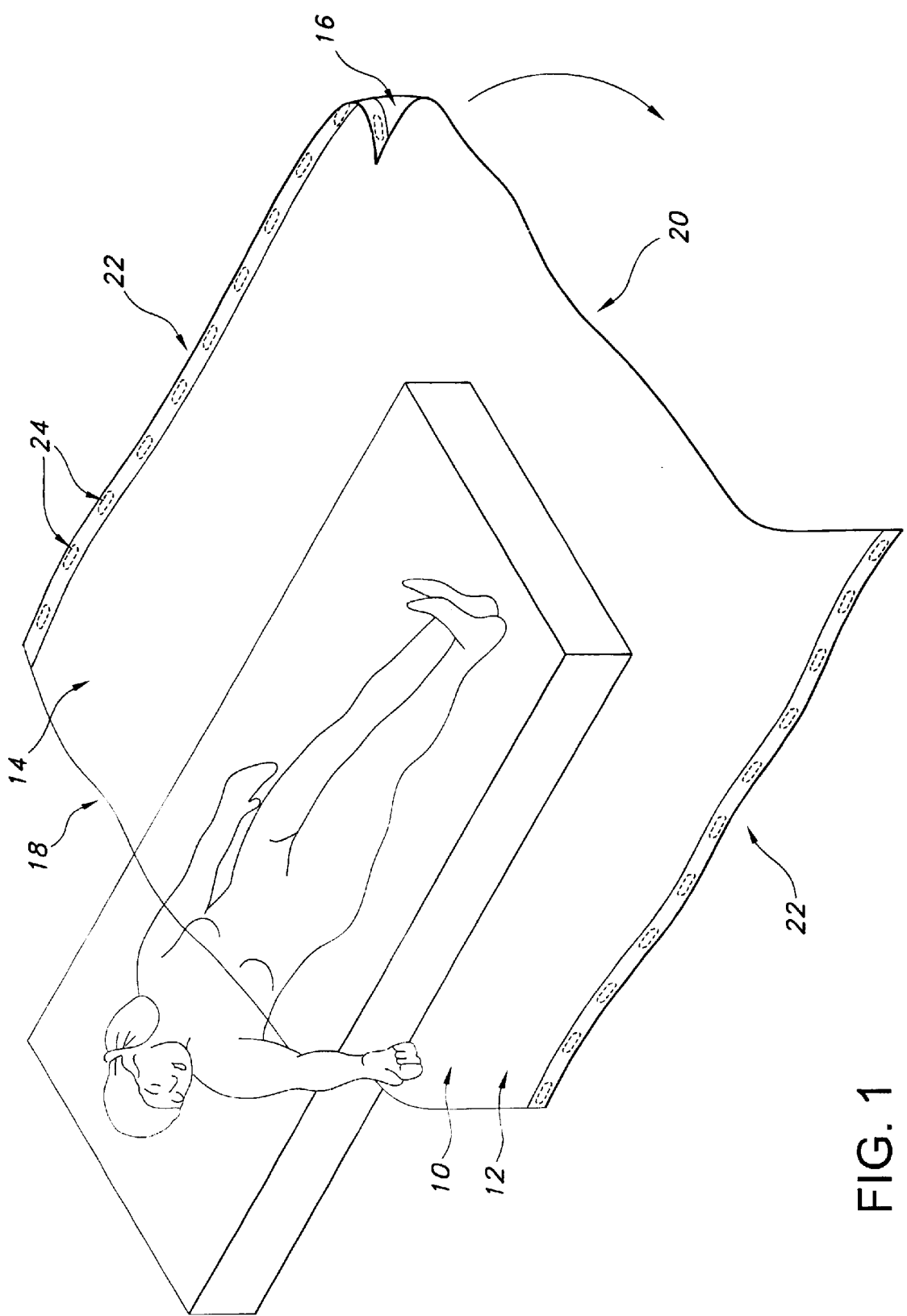
FIG. 1 shows an embodiment of a drape in accordance with the present invention.

The present invention and its advantages are best understood by referring to the drawings, like numerals being used for like and corresponding parts of the various drawings. The present invention is directed toward a weighted drape that minimizes direct user manipulation to completely unfold the drape into a configuration suitable for use in surgical procedures and aids in maintaining the unfolded edges of the drape in a stationary position thus resisting movement against unintentional contact by an operating room attendant, air drafts, etc. By adding a modest amount of weight to the edges of a drape manufactured from fabrics or webs containing meltspun polymers (polyolefins) and no cellulose, the drape unfolds better and unintentional creases are minimized due to the effects of gravity.

The surgical drape 10 of the present invention is illustrated in FIG. 1 and includes a base sheet 12 having an upper surface 14 and a lower or patient-contacting surface 16. Although it is to be understood that the drape 10 may have varying dimensions and shapes, for ease of description, the drape 10 will be referred to as being rectangular and sized to cover at least a majority of a patient's body during a surgical procedure.

The base sheet 12 may be made from a wide variety of non-cellulose containing materials, including, for example, nonwoven disposable fabrics and/or webs. Nonwoven materials suitable for use with the present invention include, for example, multilayer laminates such as a spunbonded/meltblown/spunbonded ("SMS") material. An example of a suitable fabric is disclosed in U.S. Pat. No. 4,041,203 to Brock et al., which is hereby incorporated by reference.

Other multilayer laminates may contain films to act as permeable fluid barriers. As such one possible multilayer laminate may include a spunbonded/meltblown/film material. An example of a suitable fabric is disclosed in U.S. Pat. No. 5,901,706 to Griesbach et al., which is hereby incorporated by reference.

As used herein the term "nonwoven fabric or web" means a web having a structure of individual fibers or threads that are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein, the term "meltspun fabric" refers to a nonwoven web of filaments or fibers, which are formed by extruding a molten thermoplastic material, or coextruding more than one molten thermoplastic material, as filaments or fibers from a plurality of fine, usually circular, capillaries in a spinneret with the diameter of the extruded filaments or fibers. Meltspun fabrics include, but are not limited to, spunbonded fabrics and meltblown fabrics and are characterized as having thermal bonding junctions throughout the fabric.

As used herein the terms "spunbonded fibers" or "spunbond fibers" refer to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al. Meltblown fibers are microfibers that may be continuous or discontinuous, are generally smaller than 10 microns in average diameter, and are generally tacky when deposited onto a collecting surface.

As used herein "multilayer laminate" means a laminate wherein some of the layers are spunbond fibers and some meltblown fibers such as a spunbond/meltblown/spunbond (SMS) laminate and others as disclosed in U.S. Pat. No. 4,041,203 to Brock et al., U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy. Multilayer laminates may also have various numbers of meltblown layers or multiple spunbond layers in many different configurations and may include other materials like films or coform materials, e.g. SMMS, SM, SFS, etc.

As used herein, the term "coform" means a process in which at least one meltblown diehead is arranged near a chute through which other materials are added to the web while it is forming. Such other materials may be pulp, superabsorbent particles, cellulose or staple fibers, for example. Coform processes are shown in commonly assigned U.S. Pat. No. 4,818,464 to Lau and U.S. Pat. No. 4,100,324 to Anderson et al. Webs produced by the coform process are generally referred to as coform materials.

As used herein, the term "machine direction" or MD means the length of a fabric in the direction in which it is produced. The term "cross machine direction" or CD means the width of fabric, i.e. a direction generally perpendicular to the MD.

As used herein and in the claims, the term "comprising" is inclusive or open-ended and does not exclude additional unrecited elements, compositional components, or method steps.

Referring again to FIG. 1, it may be seen that the base sheet 12 comprises a top edge 18, a bottom edge 20, and side edges 22. In the configuration shown, i.e., a rectangular drape 10, two side edges 22 are present. However, in other possible drape constructions covered herein additional edge configurations are contemplated.

Adjoined to and/or contained within opposing side edges 22 is a source of additional weight. The source is uniformly distributed along the side edges 22 in such a way that the drape 10 when placed over a user unfolds in a substantially vertical fashion under the influence of gravity. The source may include but is not limited to a plurality of individual components 24 such as metal, ceramic, plastic, rubber, or composites configured into masses, ingots, or the like.

Figure 2:
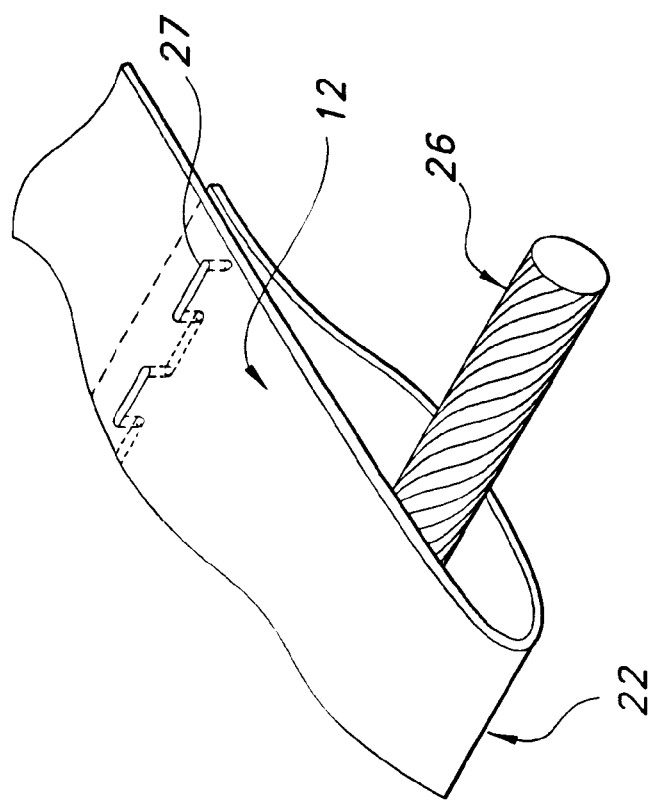
FIG. 2 shows an alternate embodiment of the FIG. 1 drape in accordance with the present invention.

Other potential embodiments such as that shown in FIG. 2 contemplate the source as being a flexible material 26 extending substantially along the entire length of each side edge 22. Some flexible materials 26 may include but are not limited to:

a length of cord, line, rope, wire, and/or tape; a strip of fabric and/or fiber; a bead or beads of hot melt adhesive, polymer filled or unfilled; organic material; and/or inorganic material adjoined to or incorporated within the edges 22 in some fashion. Some methods of attaching these materials 26 to the edges 22 may include applying an adhesive to secure the material to the base sheet 12, incorporating the material into a seam 27 (as depicted), by incorporating the material into the drape itself, and/or attaching the material 26 to the edges 22 in such a way that the added material itself forms the bottom side edges of the drape 10.

Figure 3:
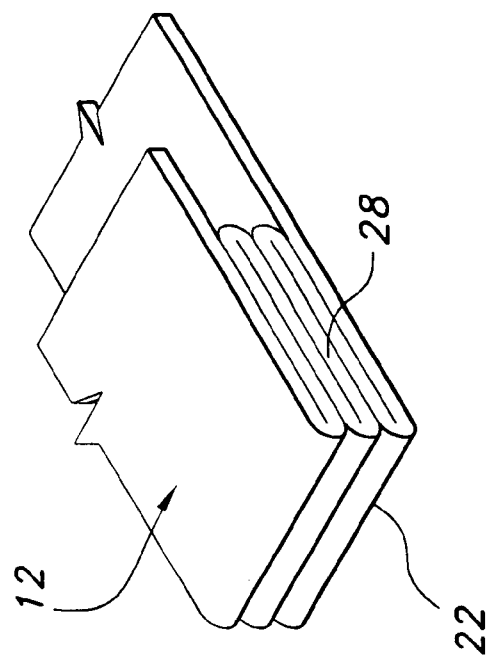
FIG. 3 shows another alternate embodiment of the FIG. 1 drape in accordance with the present invention.

Still other embodiments such as that shown in FIG. 3 contemplate the source as comprising an overfolded region or hem 28 at the edges 22. By folding the base sheet 12 repeatedly over upon itself and securing it in this manner the side edges 22 are effectively weighted. Some fold patterns contemplated may include a pleat or a plicate fold (as shown), i.e., an accordion-type overfolding of the base sheet 12. In some embodiments the fold is maintained by stitching the overfolded region together, by applying an adhesive to maintain the fold, as well as through the use of other suitable techniques known to those of skill in the art. Combinations of any of the above techniques to maintain the fold are also possible.

Some embodiments contemplate a combination of sources of additional weight. For example, one possible embodiment contemplates the addition of a plurality of individual components 24 combined with the overfolded region 28. Another embodiment contemplates the addition of a flexible material 26 incorporated into the drape 10 in addition to the overfolded region 28. Of course, the individual components 24, flexible material 26, and overfolded region 28 can be combined In any manner. In any of the embodiments, the individual components 24 and/or the flexible material 26 may be integrated into the overfolded region 28 itself. Of course other sources of additional weight are contemplated and are limited only by the knowledge of those having ordinary skill in the art.

Regardless of the form of the source of additional weight, some embodiments contemplate that the source comprise a mass per unit length of between about three times to about five times the basis weight of the base sheet 12. Other embodiments contemplate as much as about ten times the basis weight of the base sheet 12. Though larger ratios between mass per unit length of the source of additional weight and the basis weight of the base sheet 12 are possible, additional problems develop if the drape 10 is made too heavy. As such, it has been found that ratios between about three times to about eight times the basis weight of the base sheet form one desirable range of embodiments that enable the drape 10 to unfold under gravity yet are not sufficiently heavy so as to raise concerns associated with the use of a heavy drape.

It has been found in some embodiments that the source is advantageously added to the side edges 22, or to within 0.8 cm of the side edges 22. Other embodiments concentrate the source of additional weight in a region between about 0.8 cm to about 2 cm of each side edge 22. Still other embodiments concentrate the source of additional weight in a region between about 2 cm to about 5 cm of each side edge 22. The source of weight may cover the entire region or may alternatively be configured in a band having a lesser dimension contained within the region.

More specifically for those embodiments comprising overfolded regions of the base sheet 12, the mass per unit length of between about three times to about five times the basis weight of the base sheet 12 may be obtained by overlapping the base sheet three to five times.

EXAMPLES

Fabrics

Four fabrics were selected for testing These fabrics were as follows:

1. 51 gsm (1.5 osy) SMS fabric used for Evolution* 4 surgical gowns sold by Kimberly-Clark
2. ~42.5 gsm (1.0 osy) SMS fabric similar to the 51 gsm SMS fabric above except for basis weight
3. ~66 gsm (1.95 osy) film/nonwoven laminate fabric used for MICROCOOL surgical gowns sold by Kimberly-Clark
4. 64 gsm (~1.88 osy) HYDROKNIT fabric used for WYPALL® X60 Teri® Manufactured Rags SOLD BY Kimberly-Clark The first three fabrics comprise meltspun fibers containing not cellulose fibers. The fourth fabric contains cellulose and forms a baseline comparison.

To demonstrate the invention, creases were formed in each of the fabrics using heat and pressure under parameters believed to simulate the conditions experienced in packaging. Samples of the above materials were unfolded in a vertical direction, that is, the creases were arranged so they laid in the horizontal plane and the fabrics were unfolded vertically about the horizontal plane. Measurements were taken with respect to the resistance to unfolding encountered in each of the fabric specimens and this information was correlated to a fabric weight.

Preparation

Strips were cut from each fabric into two sizes such that the length direction corresponded to the "machine direction" of the fabric:
4" wide×6" long
2" wide×6" long Regardless of the width of any strip, the fabric was folded lengthwise in half so as to position a crease 3" from either end. Each crease was formed by placing the sample between flat 5"×7" aluminum plates heated to a set point temperature of 150° F., pressing the plates together, and maintaining a constant force on the plates for 10 seconds; afterwards the force was released and the sample removed. For all samples, the temperature conditions and methodology to position the sample between the plates, apply force, and remove the sample from the plates were the same. The force applied was either 5000 or 2500 pound force (created by a hydraulic ram apparatus).

Vertical Unfolding Measurements

To evaluate the fold characteristics, each creased sample was held in such a way that gravity was the only force used to unfold the fabric. A depiction of this can be seen by turning to FIGS. 4*a–d*. A folded sample 30 was positioned against a vertical wall 32 with a creased edge or fold 34 oriented in a downward position with both ends 36, 38 of the sample 30 oriented in an upward direction. The end 36 in direct contact with the wall 32 was affixed in place while the other end 38 was released. As shown in FIGS. 4*b–d*, the unfolding of each sample 30 was measured as an angle α separating each of the ends 36 and 38. The angle α was correlated to an opening of less than (<) 90° from vertical as shown in FIG. 4*b*, of more than (>) 90° from vertical as shown in FIG. 4*c*, or being substantially equal to (=) 90° from vertical as shown in FIG. 4*d*.

When the released end 38 was 3" long as measured from the crease 34 all samples unfolded to an angle α greater than 90° from the vertical. It was concluded that the total weight of the fabric between the crease 34 and the end 38 was sufficient to overcome the tendency for the crease 34 angle α to remain less than 90° from the vertical.

To determine the amount of weight needed to unfold the crease to an angle α of substantially equal to or greater than 90° from vertical the length of the released end 38 was shortened incrementally by an inch to two inches and subsequently to one inch. Finally, each sample was shortened by 0.5 inch increment to 0.5 inch. For a given material, no difference in unfolding was observed between the 2 inch and 4 inch wide strips. Therefore it was determined that the unit width of the samples had little effect on the results. Table 1 compares the unfolding characteristics that were repeatedly observed in the samples:

TABLE 1

| Sample | Sample Width | 2" End | 1" End | 0.5" End |
| --- | --- | --- | --- | --- |
| 1.5 SMS at 5000 lb ram | 4" | >90° | =90° | <90° |
| 1.5 SMS at 5000 lb ram | 2" | >90° | < or =90° | — |
| 1.5 SMS at 2500 lb ram | 2" | >90° | < or >90° | <90° |
| 1.0 SMS at 5000 lb ram | 2" | >90° | < or =90° | — |
| 1.0 SMS at 2500 lb ram | 4" | >90° | =90° | — |
| MICROCOOL at 5000 lb ram | 4" | >90° | <90° | — |
| MICROCOOL at 5000 lb ram | 2" | >90° | <90° | — |
| MICROCOOL at 2500 lb ram | 2" | >90° | <90° | — |
| WYPALL 60X at 5000 lb ram | 2" | <90° | — | — |

Translating the fabric contribution into weight at the edge of the fold is determined by the following formula $$\frac{(\text{Basis Weight of Fabric}) \times (\text{Area below the Fold})}{\text{Length of Fold}}$$

Or, for the case of the fabric used in the example, where:

Area below the Fold=(Length of End)×(Width of End)

Length of Fold=Width of End

The fabric contribution into weight at the edge of the fold or the effective weight below the fold equals:

(Basis Weight of the Fabric)×(Length of End)

And for the materials measured, are:

| Sample | Effective Weight Below the Fold g/cm | | |
|---|---|---|---|
| | 2" End | 1" End | 0.5" End |
| 1.5 SMS | 0.025908 | 0.0129538 | 0.0064769 |
| 1.0 SMS | 0.02159 | 0.010795 | 0.0053975 |
| MICROCOOL | 0.0335275 | 0.0167637 | 0.0083819 |
| WYPALL 60X | 0.0325115 | 0.0162557 | 0.0081279 |

While the invention has been described in detail with respect to specific preferred embodiments thereof, it will be appreciated that those skilled in the art, upon attaining an understanding of the foregoing, may readily conceive of alterations to and variations of the preferred embodiments. Such alterations and variations are believed to fall within the scope and spirit of the invention and the appended claims.

What is claimed is:

1. A nonwoven surgical drape comprising a non-cellulose base sheet including a top edge, a bottom edge, at least two side edges, and a source of additional weight uniformly distributed along the side edges, the source having a mass per unit length between about three times and about eight times the basis weight of the base sheet.

2. The drape of claim 1 wherein the source is within about 2 cm to about 5 cm of each side edge.

3. The drape of claim 1 wherein the source is within about 0.8 cm to about 2 cm of each side edge.

4. The drape of claim 1 wherein the source is within about 0.8 cm of each side edge.

5. The drape of claim 1 wherein the source is uniformly divided along each side edge.

6. The drape of claim 1 wherein the source comprises a flexible material adjoined to each side edge.

7. The drape of claim 1 wherein the source comprises a bead of hot melt adhesive.

8. The drape of claim 7 wherein an organic matter is encompassed within the adhesive.

9. The drape of claim 7 wherein an inorganic matter is encompassed within the adhesive.

10. The drape of claim 1 wherein the source comprises a flexible filled-polymer band.

11. The drape of claim 1 wherein the source comprises a nonabsorbent material.

12. A nonwoven surgical drape comprising a base sheet having a top edge, a bottom edge, at least two side edges, and a nonabsorbent material uniformly distributed along at least the side edges, the nonabsorbent material having a basis weight at least equal to about three times the basis weight of the base sheet.

13. The drape of claim 12 wherein the nonabsorbent material is within about 2 cm to about 5 cm of each side edge.

14. The drape of claim 12 wherein the nonabsorbent material is within about 0.8 cm to about 2 cm of each side edge.

15. The drape of claim 12 wherein the nonabsorbent material is within about 0.8 cm of each side edge.

16. The drape of claim 12 wherein the nonabsorbent material comprises a flexible material adjoined to each side edge.

* * * * *